United States Patent [19]

Kelly

[11] 4,083,854

[45] Apr. 11, 1978

[54] 4,5-DIDEHYDRO-6-OXO-2-ARYL-METHOXYMETHYL-3α-TETRAHYDROPYRANACETIC ACIDS

[75] Inventor: Robert C. Kelly, Kalamazoo, Mich.

[73] Assignee: The Upjohn Company, Kalamazoo, Mich.

[21] Appl. No.: 784,475

[22] Filed: Apr. 4, 1977

Related U.S. Application Data

[62] Division of Ser. No. 676,890, Apr. 14, 1976, Pat. No. 4,020,173.

[51] Int. Cl.$^2$ .................................... C07D 309/32
[52] U.S. Cl. .................................... 260/343.5
[58] Field of Search .................................... 260/343.5

[56] References Cited

U.S. PATENT DOCUMENTS

| | | | |
|---|---|---|---|
| 4,032,542 | 6/1977 | Kelly | 260/343.6 |
| 4,048,194 | 9/1977 | Nelson | 260/343.6 |

*Primary Examiner*—Cecilia M. Jaisle
*Attorney, Agent, or Firm*—Robert A. Armitage

[57] ABSTRACT

The present specification provides novel intermediates and novel processes for the synthesis of Thromboxane B$_2$ (11a-homo-11a-oxa-PGF$_{2\alpha}$), its 15-epimer, and various carboxyl derivatives thereof. In particular, there are disclosed various bicyclic tetrahydrofuran-containing lactones useful in the above processes, and corresponding acyclic lactones.

2 Claims, No Drawings

4,5-DIDEHYDRO-6-OXO-2-ARYL-METHOX-YMETHYL-3α-TETRAHYDROPYRANACETIC ACIDS

The present application is a divisional application of Ser. No. 676,890, filed Apr. 14, 1976, now issued as U.S. Pat. No. 4,020,173 on Apr. 26, 1977.

The present invention relates to Thromboxane $B_2$ and associated intermediates and processes, for which the essential material constituting disclosure therefor is incorporated by reference here from Ser. No. 676,890, filed Apr. 14, 1976, now issued as U.S. Pat. No. 4,020,173 on Apr. 26, 1977.

I claim:

1. A thromboxane intermediate of the formula

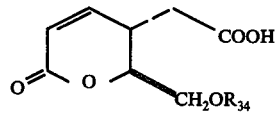

wherein $R_{34}$ is an arylmethyl hydroxy-hydrogen replacing group selected from the group consisting of
   (a) benzyl,
   (b) benzyl substituted by one to five alkyl of one to four carbon atoms, inclusive, chloro, bromo, iodo, fluoro, nitro, phenylalkyl of 7 to 12 carbon atoms, inclusive,
   (c) benzhydryl,
   (d) benzhydryl substituted by one to ten alkyl of one to four carbon atoms, inclusive, chloro, bromo, iodo, fluoro, nitro, phenylalkyl of 7 to 12 carbon atoms, inclusive,
   (e) trityl, and
   (f) trityl substituted by one to 15 alkyl of one to four carbon atoms, inclusive, chloro, bromo, iodo, fluoro, nitro, phenylalkyl of 7 to 12 carbon atoms, inclusive.

2. 4,5-Didehydro-6-oxo-2β-benzyloxymethyl-3α-tetrahydropyranacetic acid, a thromboxane intermediate according to claim 1.

* * * * *

UNITED STATES PATENT OFFICE
CERTIFICATE OF CORRECTION

Patent No. 4,083,854  Dated April 11, 1978

Inventor(s) Robert C. Kelly

It is certified that error appears in the above-identified patent and that said Letters Patent are hereby corrected as shown below:

[62] should read -- Division of Serial No. 676,895, April 14, 1976, Patent No. 4,032,542 -- instead of as shown on the patent.

Column 1, lines 12 and 14 should read -- Serial No. 676,895, filed April 14, 1976, now issued as U.S. Patent No. 4,032,542 on June 28, 1977.-- instead of as shown in the patent.

Signed and Sealed this

Thirty-first Day of October 1978

[SEAL]

Attest:

RUTH C. MASON
Attesting Officer

DONALD W. BANNER
Commissioner of Patents and Trademarks